(12) United States Patent
Kocur (10) Patent No.: US 9,198,657 B2
(45) Date of Patent: Dec. 1, 2015

(54) ANCHOR UNIT IMPLANT (76) Inventor: Basil Anthony Kocur, Bronxville, NY (US)

( * ) Notice: Subject to any disclaimer, the term of this patent is extended or adjusted under 35 U.S.C. 154(b) by 469 days.

(21) Appl. No.: 13/614,030

(22) Filed: Sep. 13, 2012

(65) Prior Publication Data

US 2014/0074121 A1  Mar. 13, 2014

(51) Int. Cl.
*A61B 17/03* (2006.01)
*A61B 17/064* (2006.01)
*A61B 17/068* (2006.01)
*A61B 17/04* (2006.01)

(52) U.S. Cl.
CPC .............. *A61B 17/064* (2013.01); *A61B 17/068* (2013.01); *A61B 2017/0412* (2013.01); *A61B 2017/0647* (2013.01)

(58) Field of Classification Search
CPC ............... A61B 2017/0412; A61B 2017/0647; A61B 17/064; A61B 17/068
USPC ................. 606/151, 213, 220, 286, 139, 185
See application file for complete search history.

(56) References Cited

U.S. PATENT DOCUMENTS

| 4,884,572 | A | 12/1989 | Bays et al. |
| 4,895,148 | A | 1/1990 | Bays et al. |
| 4,924,865 | A | 5/1990 | Bays et al. |
| 4,976,715 | A | 12/1990 | Bays et al. |
| 5,013,316 | A | 5/1991 | Goble et al. |
| 5,059,206 | A | 10/1991 | Winters |
| 5,129,906 | A | 7/1992 | Ross et al. |
| 5,203,784 | A | 4/1993 | Ross et al. |
| 5,246,441 | A | 9/1993 | Ross et al. |
| 5,643,319 | A | 7/1997 | Green et al. |
| 5,749,899 | A | 5/1998 | Bardin |
| 5,948,000 | A | 9/1999 | Larsen et al. |
| 5,954,747 | A * | 9/1999 | Clark .............................. 606/216 |
| 6,056,751 | A * | 5/2000 | Fenton, Jr. ....................... 606/28 |
| 6,083,238 | A * | 7/2000 | Alexander et al. ............. 606/185 |
| 6,096,060 | A | 8/2000 | Fitts et al. |
| 6,146,387 | A | 11/2000 | Trott et al. |
| 6,190,401 | B1 | 2/2001 | Green et al. |
| 6,387,113 | B1 | 5/2002 | Hawkins et al. |
| 6,511,481 | B2 * | 1/2003 | von Hoffmann et al. ........ 606/67 |
| 6,551,343 | B1 * | 4/2003 | Tormala et al. ................ 606/213 |
| 6,616,665 | B2 | 9/2003 | Grafton et al. |
| 7,670,362 | B2 | 3/2010 | Zergiebel |
| 7,758,612 | B2 | 7/2010 | Shipp |
| 7,862,573 | B2 | 1/2011 | Darois et al. |
| 7,867,264 | B2 | 1/2011 | McDevitt et al. |
| 8,002,811 | B2 | 8/2011 | Corradi et al. |
| 2002/0183762 | A1 | 12/2002 | Anderson et al. |
| 2003/0078604 | A1* | 4/2003 | Walshe ............................ 606/151 |
| 2003/0105477 | A1 | 6/2003 | Schwartz et al. |

(Continued)

*Primary Examiner* — Thomas McEvoy
*Assistant Examiner* — Julie A Szpira
(74) *Attorney, Agent, or Firm* — Law Office of Peter G. Korytnyk, PLLC (57) ABSTRACT

An anchor unit, an instrument for deploying the anchor unit, and methods of treating or preventing vaginal vault prolapse and/or uterine prolapse in conditions of utero-vaginal prolapse are disclosed. The anchor unit can include an anchor housing and an anchor blade assembly. The anchor housing can include a first peripheral wall and a second peripheral wall which can be arranged in the shape of a knife blade. The anchor blade assembly can include a plurality of blades for securing the anchor unit to body tissue. The anchor blade assembly can be configured to be rotatable with respect to the anchor housing to allow the deployment of the plurality of blades into body tissue in a deployed state of the anchor unit.

11 Claims, 7 Drawing Sheets

(56) References Cited

U.S. PATENT DOCUMENTS

| | | |
|---|---|---|
| 2006/0089525 A1 | 4/2006 | Mamo et al. |
| 2006/0235410 A1* | 10/2006 | Ralph et al. .................. 606/72 |
| 2007/0142846 A1* | 6/2007 | Catanese et al. .............. 606/142 |
| 2007/0270893 A1* | 11/2007 | Pikus et al. .................. 606/159 |
| 2009/0204130 A1* | 8/2009 | Kantsevoy et al. ............ 606/151 |
| 2010/0022822 A1* | 1/2010 | Walshe ........................... 600/37 |
| 2011/0092992 A1* | 4/2011 | Darois et al. .................. 606/151 |
| 2011/0160529 A1 | 6/2011 | Crawford |
| 2012/0172931 A1* | 7/2012 | Ben Rubi ....................... 606/228 |
| 2012/0203261 A1* | 8/2012 | Au et al. ....................... 606/185 |
| 2012/0203340 A1* | 8/2012 | Choinski et al. ............ 623/13.14 |

* cited by examiner

ANCHOR UNIT IMPLANT

FIELD OF THE INVENTION

The present teachings relate to anchor devices and instruments that can be used to repair body tissue. In particular, the present teachings relate to an absorbable anchor device, an instrument to deploy an anchor device, and methods of repairing body tissue for treating or preventing, for example, vaginal vault prolapse.

BACKGROUND OF THE INVENTION

Surgical methods for suspending a prolapsed vagina (also known as fallen vagina) to the sacrospinous ligament and/or the iliococcygeus muscle and fascia to surgically correct vaginal vault prolapse are well documented. Such suspensions have been well-described and studied in the literature using both absorbable and non-absorbable sutures.

For example, a transvaginal surgical approach for the treatment of utero-vaginal and vaginal vault prolapse has been used for decades. This vaginal approach still uses sutures to suspend the vagina to either the sacrospinous ligament, cardinal ligament, or to the iliococcygeus muscle and fascia. More recently, transvaginal techniques have used trochars to insert mesh to support the uterus and/or vagina but these techniques have been found to have undesirable postoperative complications, including mesh erosion, pelvic pain, and pain with sexual relations. There are also known transabdominal and laproscopic procedures that are performed to suspend the prolapsed organs to the sacral promontory (i.e. the upper part of the tail bone) using a piece of mesh as a bridge between the two fixation sites. These procedures require general anesthesia and single or multiple abdominal incisions and have a risk of vaginal mesh erosion, as well as bowel mesh entrapment or erosion with resultant bowel perforation and obstruction.

In the transvaginal approach, using various suture delivery systems requires opening the posterior or anterior vaginal wall, and extensive dissection into perirectal space to reach the appropriate desired fixation site. The surgery is deep within the pelvis, is difficult to perform, and requires surgical experience and training. When using sutures that absorb, the fixation site on the vaginal side can go into and through the vaginal wall or, if using a permanent suture, must be buried beneath the vaginal wall so as not to erode through the vaginal wall. Delayed absorbable sutures can also be placed without a vaginal incision by placing them through the appropriate area in the vaginal wall into the iliococcygeus muscle and fascia and back out into the vagina and then tying them. Unfortunately, because of the curve of the needle, appropriate and especially adequate placement into the muscle and its fascia is difficult.

In the transvaginal approach, the suspension to the sacrospinous ligament is considered the gold standard. The problem with this suspension is that it is usually performed only on the patient's right side, as the sigmoid colon on the patient's left may be injured during dissection. This unilateral suspension causes the vagina on that side to be pulled to the right side which can lead to vaginal narrowing, shortening and stenosis if too much vaginal wall is excised. This can lead to pelvic pain and pain with sexual relations. If the vagina is very wide at the top after a unilateral suspension, it can expose the opposite unsuspended vaginal wall to excessive downward force that may lead to prolapse. Moreover, whether using one or two permanent or absorbable sutures in the suspension, these stitches may tear leading to recurrent prolapse.

Accordingly, there exists a need for a device and method that can be used to readily and easily support one or both sides of the vaginal wall to the iliococcygeus muscle and fascia and/or the sacrospinous ligament without necessitating opening the vaginal wall and dissecting into the perirectal space.

SUMMARY OF THE INVENTION

The present teachings provide an anchor unit for the repair of body tissue. The anchor unit can include an anchor housing having a first peripheral wall and a second peripheral wall. The first peripheral wall and the second peripheral wall can be arranged in the shape of a knife blade. The anchor unit can also include an anchor blade assembly arranged with the anchor housing and including a plurality of deployable blades for securing the anchor unit to body tissue in a deployed state.

The present teachings also provide an instrument for manipulating an anchor unit in body tissue. The instrument can include a barrel having a guiding slot and a plunger arrangement configured to reciprocate and rotate with respect to the guiding slot. A trigger can be configured to reciprocate the plunger arrangement within the guiding slot of the barrel. A turning knob can be configured to rotate a portion of the plunger arrangement with respect to the barrel. The plunger arrangement can include a distal end which is configured to operatively attach with an anchor unit so as to be capable of linearly translating and rotating a portion of the anchor unit by way of actuation of the trigger and the turning knob.

The present teachings provide a further instrument for deploying an anchor unit into body tissue. The instrument can include a barrel including a guiding slot and a plunger arrangement configured to reciprocate and rotate with respect to the guiding slot. A trigger can be configured to reciprocate the plunger arrangement within the guiding slot of the barrel. A turning knob can be configured to rotate a portion of the plunger arrangement with respect to the barrel. The plunger arrangement can include a distal end which is configured to operatively engage with an anchor blade assembly of an anchor unit. The anchor unit can include an anchor housing rotatably supporting the anchor blade assembly whereby the distal end of the plunger arrangement is capable of rotating the anchor blade assembly with respect to the anchor housing.

The present teachings still further provide a method of repairing body tissue. The method can include providing an anchor unit, the anchor unit including an anchor housing having a base and an anchor blade assembly rotatably supported by the anchor housing. The method can further include placing the anchor unit at a location where a repair of body tissue is desired and inserting the anchor unit at the desired location through a tissue wall and into tissue on the other side of the wall. The method can still further include rotating the anchor blade assembly with respect to the anchor housing to deploy the anchor unit.

The present teachings even further provide a method of treating or preventing vaginal vault prolapse. The method can include providing an anchor unit, the anchor unit including an anchor housing and an anchor blade assembly. The method can further include placing the anchor unit at a desired location on a prolapsed vaginal wall to be repaired and inserting the anchor unit at the desired location through the vaginal wall and into the iliococcygeus muscle and fascia and/or sacrospinous ligament on the other side of the vaginal wall.

Additional features and advantages of various embodiments will be set forth, in part, in the description that follows, and will, in part, be apparent from the description, or may be learned by the practice of various embodiments. The objectives and other advantages of various embodiments will be

It is to be understood that both the foregoing general description and the following detailed description are exemplary and explanatory only, and are intended to provide an explanation of various embodiments of the present teachings.

DETAILED DESCRIPTION OF THE PREFERRED EMBODIMENTS

The present teachings relate to devices, instruments, and methods for treating or preventing vaginal vault prolapse through the use of anchors. In particular, the present teachings relate to an absorbable anchor unit 30 and an instrument 100 for transvaginally delivering the absorbable anchor unit 30 into and through the vaginal wall and into the iliococcygeus muscle and fascia and/or the sacrosipnous ligament without having to open and dissect the vaginal wall. The anchor unit 30 of the present teachings includes blades that when deployed, penetrate into tissue to hold the anchor unit 30 in place. The anchor unit 30 can be used to secure and suspend a vaginal wall to muscle, fascia or ligaments to correct the prolapse. The anchor unit 30 can also be used to secure and suspend various other types of tissue and can be deployed using various different instruments. The anchor unit 30 of the present teachings can be designed to eventually dissolve leaving behind enough scarring to hold the vaginal wall in proper position. The present teachings also relate to a primary surgical procedure for the repair of diagnosed vaginal vault prolapse and to the repair and/or prevention of vaginal vault prolapse diagnosed at the time of vaginal hysterectomy and/or prolapse repair. In addition, the present teachings relate to a primary surgical procedure to treat and prevent uterine prolapse at the time of prolapse repair.

Figures 1A, 1B:
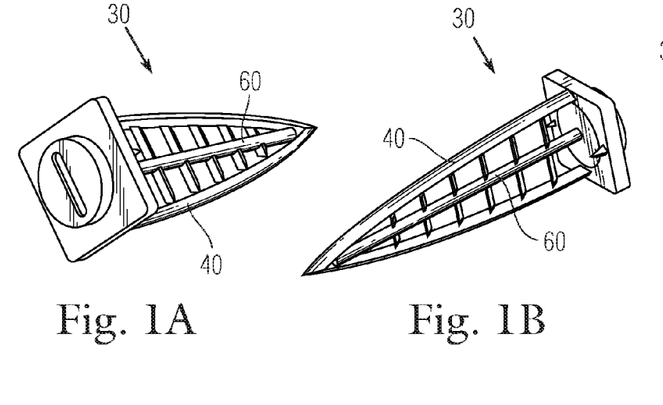
FIGS. 1A, 1B, and 1C are each different perspective views of the anchor unit according to the present teachings.
Figure 1C:
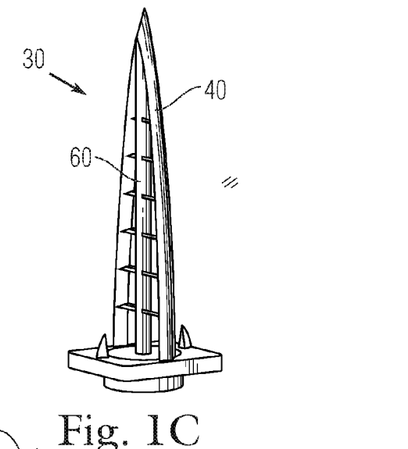

Referring to FIGS. 1A-1C, a non-deployed anchor unit 30 of the present teachings is shown. The anchor unit 30 can include at least two components. A first component can include an outer anchor housing 40. The second component can include an anchor blade assembly 60. The anchor blade assembly 60 can be arranged to be supported by the outer anchor housing 40. As will be disclosed more fully below, the anchor blade assembly 60 can be arranged to translate or rotate with respect to the outer anchor housing 40 to place the anchor unit 30 in either a deployed or non-deployed state. More particularly, the anchor blade assembly 60 can be arranged to rotate generally within the outer anchor housing 40.

Each of the outer anchor housing 40 and the anchor blade assembly 60 can be made of any length and can be made from a biodegradable polymer or a copolymer of the type selected in accordance with the desired degradation time. The desired degradation time depends upon the anticipated healing time for the type of tissue which is the subject of the surgical procedure. Known biodegradable polymers and copolymers range in degradation time from about 3 months for polyglycolide to about 48 months for polyglutmic-co-leucine.

In an exemplary embodiment, one or more of the components of the absorbable anchor unit 30 can be made in part, or made entirely from, polydioxanone (or similar material) with or without infused polyglactin 910 (or similar material).

The following is a list of biodegradable polymers (and copolymers and terpolymers thereof) that can be employed in making the anchor unit 30 of the present teachings: polycaprolactone, poly(L-lactide), poly(DL-lactide), polyglycolide, 95:5 poly(DL-lactide-co-glycolide), 90:10 poly(DL-lactide-co-glycolide), 85:15 poly(DL-lactide-co-glycolide), 75:25 poly(DL-lactide-co-glycolide), 50:50 poly(DL-lactide-co-glycolide), 90:10 poly(DL-lactide-co-caprolactone), 75:25 poly(DL-lactide-co-caprolactone), 50:50 poly(DL-lactide-co-caprolactone), polydioxanone, polyesteramides, copolyoxalates, polycarbonates, and poly(glutamic-co-leucine). It is also contemplated that the anchor unit 30 of the present teachings can be made of other polymers or copolymers that are biodegradable.

Figures 2A, 2B, 2C:
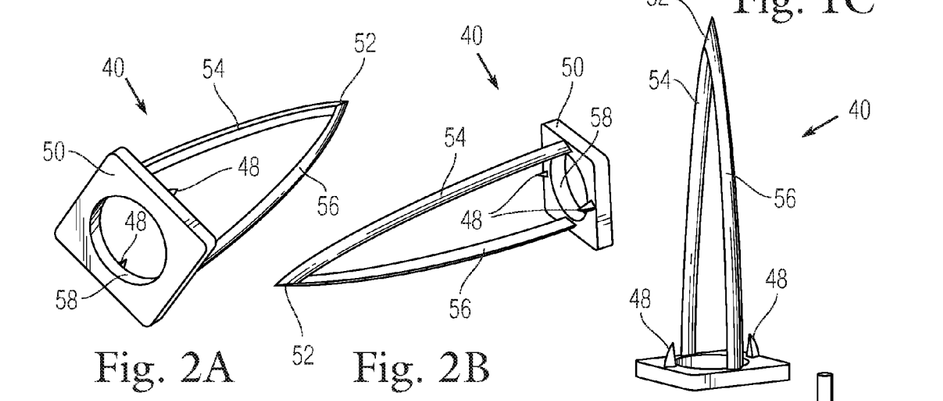
FIGS. 2A, 2B, and 2C are each different perspective views of the outer anchor housing of the anchor unit according to the present teachings.

As shown in FIGS. 2A-2C, the outer anchor housing 40 can be in the form of a symmetrical knife blade having a sharp tip 52 on a distal end thereof and sharp edges along respective outer peripheral walls 54, 56. The outer peripheral walls 54, 56 of the outer anchor housing 40 can extend outwardly from an anchor base 50 and can meet at the sharp tip 52 of the outer anchor housing 40. However, the outer anchor housing 40 can take any form that can penetrate into body tissue.

One or more protuberances or spikes 48 can be formed in the anchor base 50. The spikes 48 can be arranged on the anchor base 50 at opposite sides of the outer peripheral walls 54, 56 of the outer anchor housing 40.

An aperture 58 can be formed in the anchor base 50. As will be discussed more fully below with respect to FIG. 4A, the aperture 58 can be threaded to receive and support the anchor blade assembly 60 within the outer anchor housing 40.

Figure 3A:
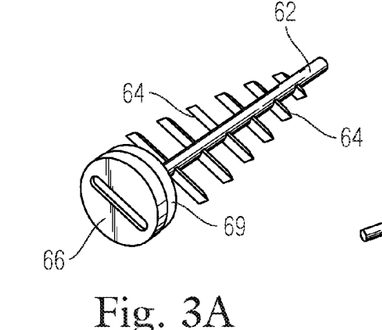
FIGS. 3A, 3B, and 3C are each different perspective views of the anchor blade assembly of the anchor unit according to the present teachings.
Figure 3B:
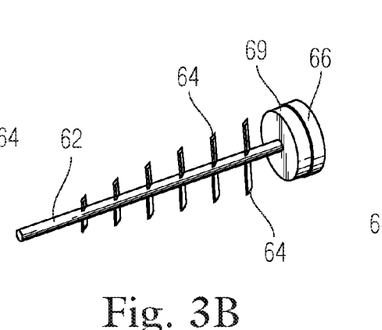
Figure 3C:
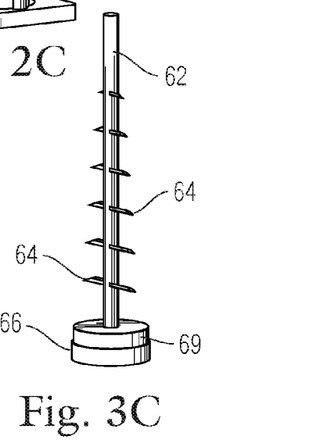

As shown in FIGS. 3A-3C, the anchor blade assembly 60 can include a head 66 and a main shaft 62 extending from the head 66. A plurality of blades or fins 64 can be arranged to extend from the vicinity of the head 66 and along the length of the main shaft 62. The plurality of blades 64 can be arranged periodically along the length of the main shaft 62. The plurality of blades 64 can be arranged to extend outwardly from the main shaft 62. The plurality of blades 64 can be arranged to extend in a co-planar manner along the length of the main shaft 62.

Figures 4A, 4B, 4C:
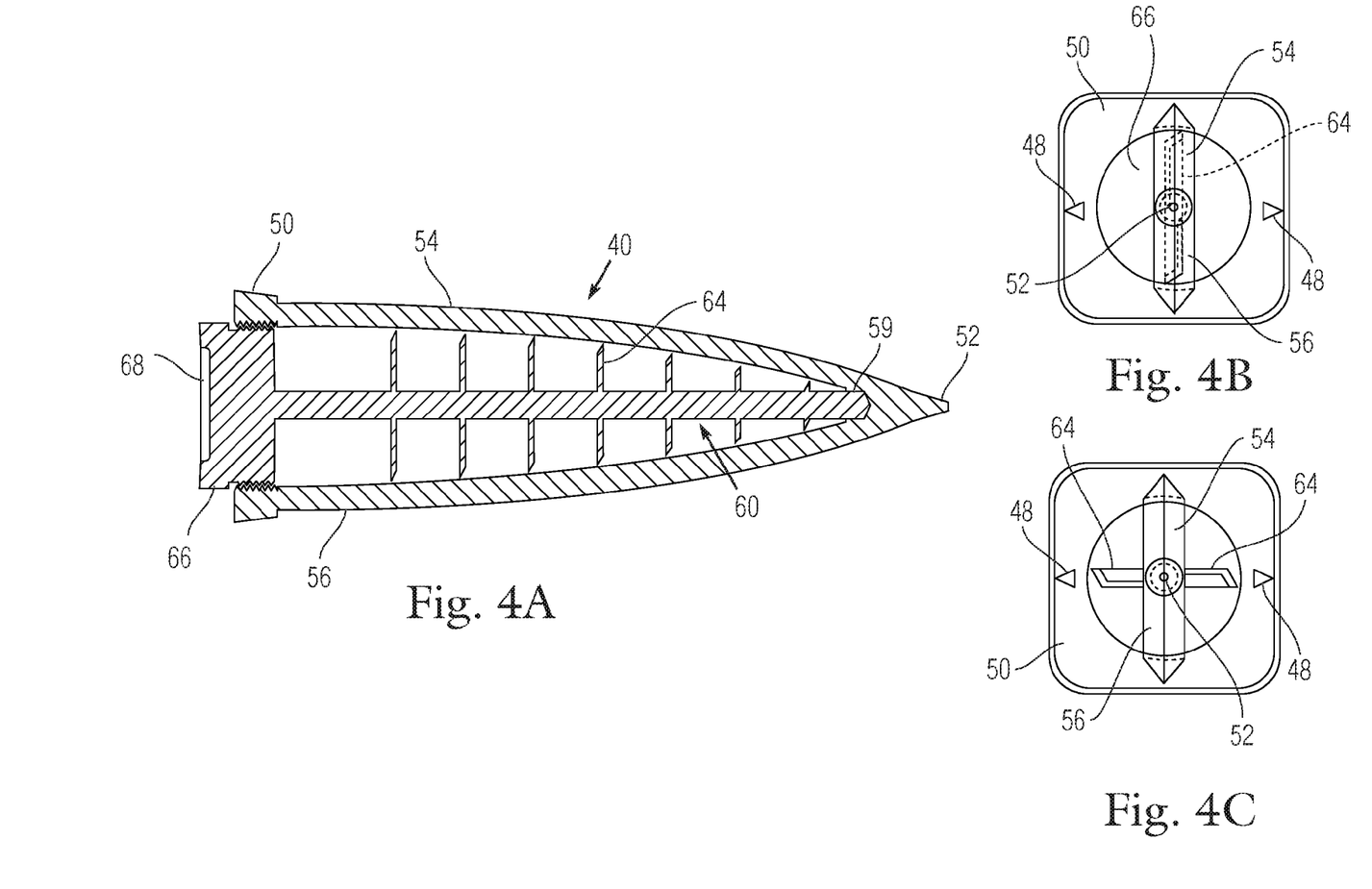
FIG. 4A is a cross-sectional side view of the anchor unit according to the present teachings.
FIG. 4B is an end view of the anchor unit in a non-deployed state of the blades according to the present teachings.
FIG. 4C is an end view of the anchor unit in a deployed state of the blades according to the present teachings.

The head 66 of the anchor blade assembly 60 can include threads 69 so as to be securable within the corresponding threaded aperture 58 of the base 50 of the outer anchor housing 40. FIG. 4A shows the head 66 of the anchor blade assembly 60 being threadingly secured to the anchor base 50 of the outer anchor housing 40. Moreover, a distal end of the main shaft 62 of the anchor blade assembly 60 can be rotatably supported in the vicinity of the sharp tip 52 of the outer anchor housing 40. For example, the distal end of the main shaft 62 can be rotatably supported in a journal bearing 59 formed in the outer peripheral walls 54, 56. In this manner, the anchor blade assembly 60 can be rotationally supported within the outer peripheral walls 54, 56 of the outer anchor housing 40.

In a non-deployed state of the blades 64, the anchor blade assembly 60 can be rotationally arranged so that the blades 64 are co-planar with the outer peripheral walls 54, 56 of the outer anchor housing 40. The non-deployed state of the anchor unit 30 can best be seen in FIGS. 1A-1C and in FIG. 4B. As shown in FIG. 4B, the blades 64 of the anchor blade assembly 60 are shown within the confines of the outer peripheral walls 54, 56 of the outer anchor housing 40.

In the non-deployed state, the anchor unit 30 of the present teachings takes the shape of a knife blade which can readily penetrate into tissue using an anchor insertion instrument 100, as will be disclosed more fully below. After being inserted into tissue, the blades 64 can be deployed by rotating the anchor blade assembly 60 a set angle with respect to the outer peripheral walls 54, 56 of the outer anchor housing 40, such as, for example, a rotation angle of about 90°. The deployed state of the anchor unit 30 is shown in FIG. 4C where the plurality of blades 64 are shown extending outwardly beyond the plane defined by the outer peripheral walls 54, 56 of the outer anchor housing 40. As will be disclosed more fully below, this will allow the blades 64 to cut into tissue and hold the anchor unit 30 in place.

The head 66 of the anchor blade assembly 60 can include a slot 68. The slot 68 can be shaped to receive a complimentary-shaped post 122. When the post 122 is inserted into the slot 68 and turned like a screwdriver, the post 122 can rotate the anchor blade assembly 60 with respect to the outer anchor housing 40, thereby deploying the blades 64 of the anchor blade assembly 60.

Figure 5:
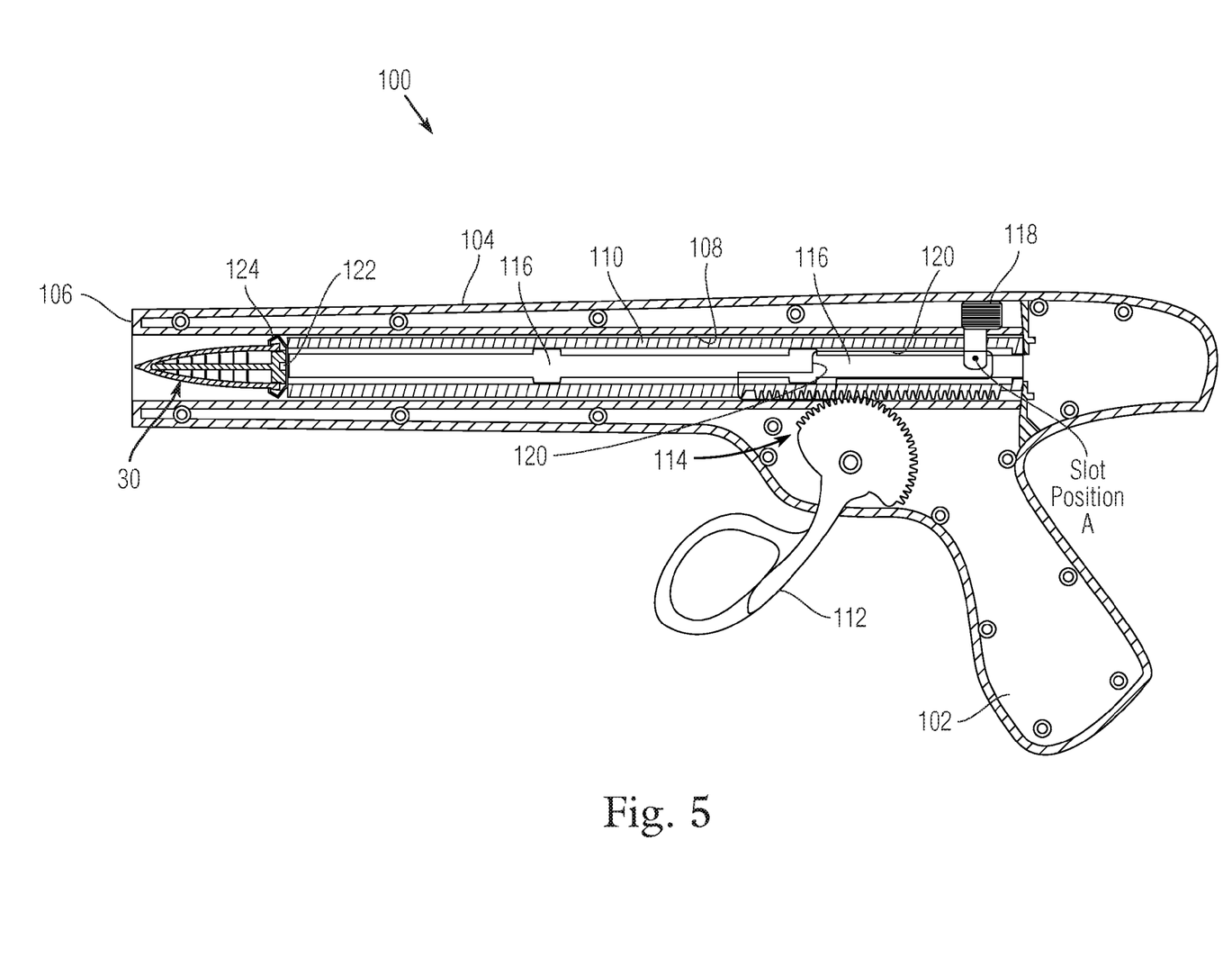
FIG. 5 is a cross-sectional side view of the tissue anchor insertion instrument of the present teachings in an anchor loaded position.
Figures 6A, 6B, 6C:
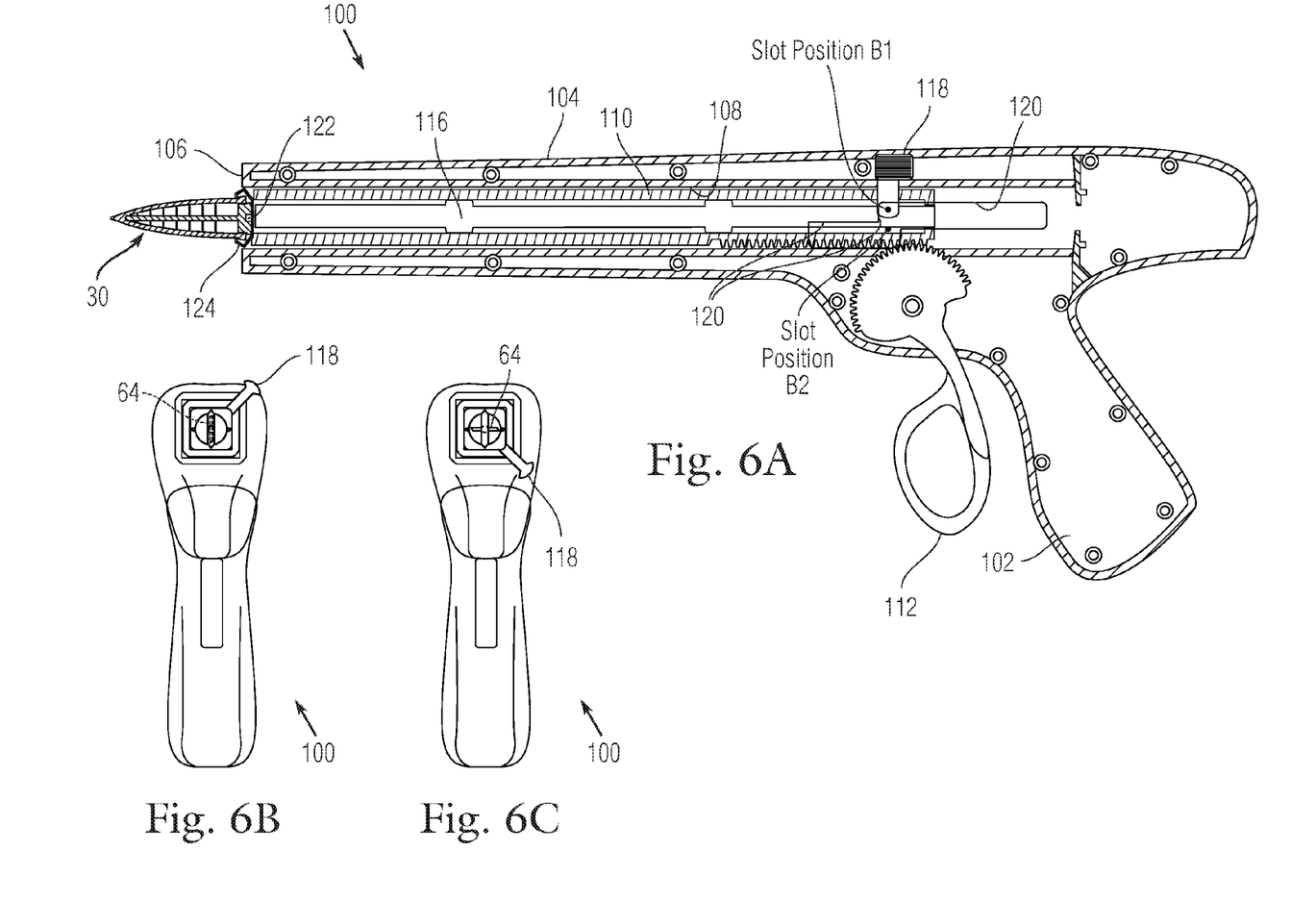
FIG. 6A is a cross-sectional side view of the tissue anchor insertion instrument of the present teachings in a nearly released position of the anchor unit.
FIGS. 6B and 6C are end views of the tissue anchor insertion instrument of the present teachings showing the turning knob in a non-deployed and deployed slot position, respectively.
Figure 7:
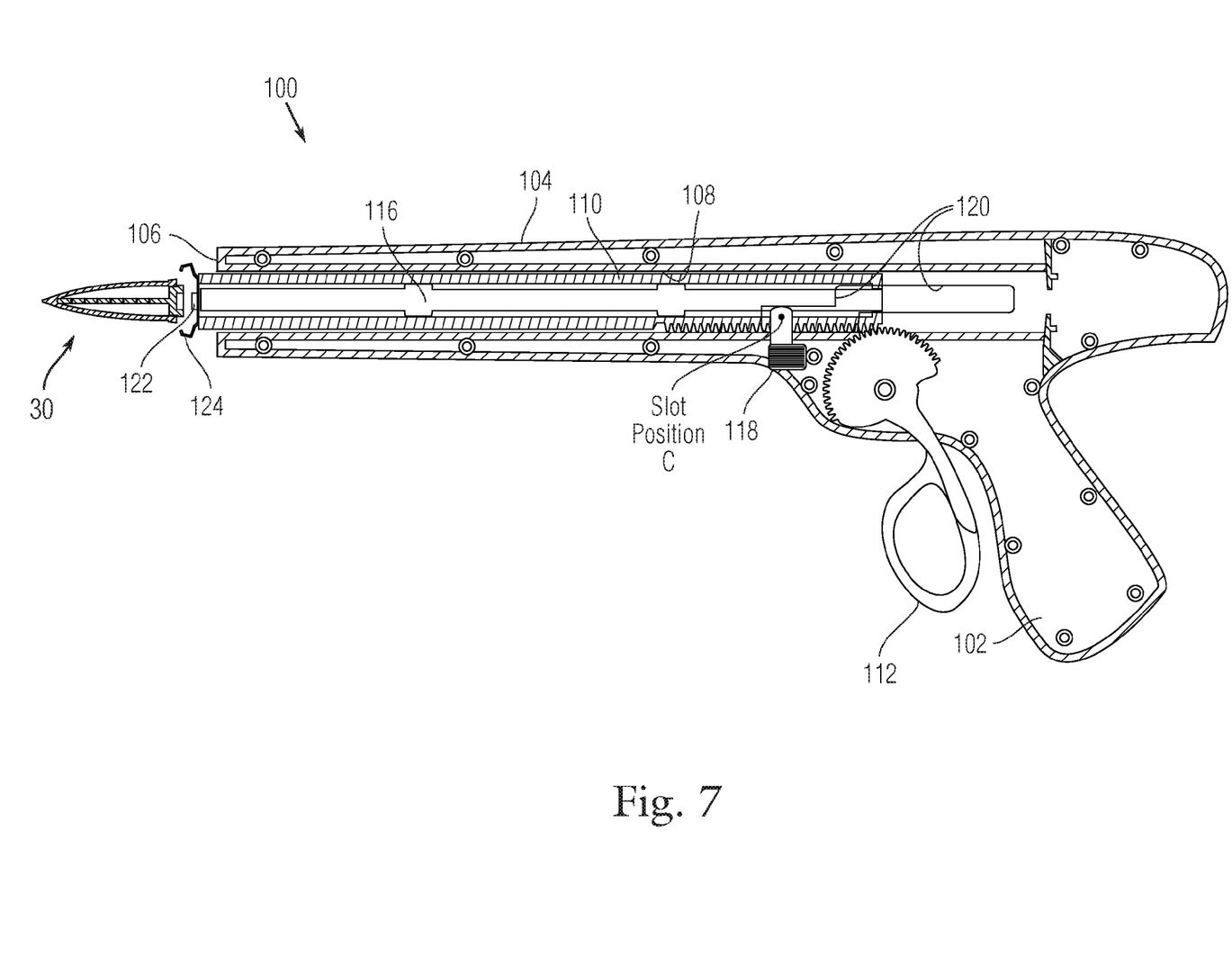
FIG. 7 is a cross-sectional side view of the tissue anchor insertion instrument of the present teachings in a released position of the anchor unit.

Referring now to FIGS. 5-7, there is disclosed a tissue anchor insertion instrument 100 for inserting and deploying an anchor unit 30. A method of using the tissue anchor insertion instrument 100 to insert an anchor unit 30 will also be disclosed.

As shown in FIG. 5, the tissue anchor insertion instrument 100 can include a handle 102, an elongated tubular barrel 104 extending from one end of the handle 102 and having a distal end 106. An interior of the barrel 104 defines a guiding slot 108 in which a plunger 110 can reciprocate. The tissue anchor insertion instrument 100 can include a user-actuable trigger lever 112 which can be operatively arranged to reciprocate the plunger 110 within the guiding slot 108 of the elongated tubular barrel 104. For example, a gearing arrangement 114 can be arranged between the trigger lever 112 and the plunger 110 for reciprocating the plunger 110. An exterior surface of the plunger 110 can include gear teeth for engagement with complimentary shaped gear teeth formed on the trigger lever 112. However, it is contemplated that any mechanism can be used to allow user-actuable movement of the plunger 110.

According to various embodiments, the plunger 110 can be arranged to have a generally square cross-sectional shape and can be arranged to reciprocate in a generally square-shape guiding slot 108. However, it is contemplated that the plunger 110 can have other cross-sectional shapes along with a corresponding shape for the guiding slot 108.

A rotatable shaft 116 can be arranged to be rotatable within the plunger 110. A user-accessible turning knob 118 can be attached to the rotatable shaft 116 for rotating the shaft 116 with respect to the plunger 110. In addition, the plunger 110 and the rotatable shaft 116 can be arranged to in reciprocate in unison with one another within the guiding slot 108 of the barrel 104 by way of the gearing arrangement 114 and by way of the user-accessible turning knob 118. The plunger 110 and the rotatable shaft 116 can together operate as a plunger arrangement within the guiding slot 108 of the elongated tubular barrel 104.

A slot 120 can be formed in the barrel 104 to allow the turning knob 118 to be accessible by the user and to provide user-controlled rotary movement of the rotatable shaft 116. The slot 120 can be generally Z-shaped as shown. A vertically extending slot (not shown) can be formed in the plunger 110. In use, the vertically extending slot in the plunger 110 can be arranged to align with a portion of the Z-shaped slot 120 in the barrel 104. In this aligned position, the turning knob 118 can extend from the rotating shaft 116 through the slot in the plunger 110 and the slot 120 in the barrel. As will be described below, this will allow the rotation of turning knob 118 from slot position B1 to slot position B2.

The post 122 can be arranged on a distal end of the rotatable shaft 116. The post 122 can be shaped so as to be insertable into the slot 68 formed in the head 66 of the anchor unit 30. Moreover, one or more clips 124 can be arranged at the distal end of the plunger arrangement. For example, the one or more clips 124 can be spring clips which can be arranged on the distal end of the plunger 110. The one or more clips 124 can be arranged to secure an anchor unit 30 to the distal end of the plunger 110 so that the anchor unit 30 can be slid forward and backward within the guiding slot 108 of the barrel 104 as the plunger 110 is reciprocated. When a clip 124 is operating to attach the anchor unit 30 to the plunger 110, the post 122 at the distal end of the rotatable shaft 116 is fitted into the slot 68 in the head 66 of the anchor unit 30.

FIG. 5 shows an anchor loaded position of the tissue anchor insertion instrument 100. In this position, the plunger 110 and the rotatable shaft 116 are in a fully-retracted position whereby the plunger arrangement is entirely situated within the barrel 104. The fully-retracted position is shown as slot position A in FIG. 5. In slot position A, the anchor unit 30 is also housed within the barrel 104.

FIG. 6A shows the tissue anchor insertion instrument 100 after the trigger lever 112 has been pulled towards the handle 102 a predetermined set distance. The predetermined set distance after which movement of the trigger lever 112 stops is shown as slot position B1. Pulling the trigger lever 112 towards the handle 102 operates to linearly translate both the plunger 110 and the rotatable shaft 116 through the guiding slot 108 of the barrel 104. Depression of the trigger lever 112 can be stopped at slot position B1, for example, by way of the turning knob 118 abutting a stop surface portion of the slot 120. At slot position B1, the attached anchor unit 30 has also been linearly translated such that the base 50 of the anchor unit 30 can be arranged flush with the tissue surface of the patient.

If the anchor unit 30 has not been inserted at the desired location on the tissue surface, the trigger lever 112 can be pushed out away from the handle 102 and so that the plunger 110 and the rotatable shaft 116 are moved back into slot position A. At this point, the distal end 106 of the tissue anchor insertion instrument 100 can then be repositioned for a further attempt to properly locate the anchor 30.

Once it has been determined that the anchor unit 30 has been inserted into the tissue at an acceptable location, the turning knob 118 can be rotated downwards to slot position B2 shown in FIG. 6A. FIGS. 6B and 6C show front views of the tissue anchor insertion instrument 100 with the turning knob 118 shown in slot position B1 and in slot position B2, respectively. Rotation of turning knob 118 from slot position B1 to slot position B2 rotates the shaft 116, which rotates the anchor blade assembly 60 a predetermined angle with respect to the outer anchor housing 40. For example, rotating turning knob 118 downwardly from slot position B1 to slot position B2 can rotate the anchor blade assembly 60 about 90° with respect to the outer anchor housing 40. Upon rotation of the anchor blade assembly 60, the plurality of blades 64 can be made to extend outwardly beyond the plane defined by the outer peripheral walls 54, 56 of the outer anchor housing 40. The deployed blades 64 can then act to cut into tissue and hold the anchor unit 30 in place. The non-deployed and deployed state of the blades 64 are shown in FIGS. 6B and 6C, as well as in FIGS. 4A-4C more fully discussed above.

If it is determined that the position of the anchor unit 30 is still not in the correct position, the turning knob 118 can be rotated back upwardly to slot position B1. Then, the trigger lever 112 can be pushed out away from the handle 102 and back into slot position A. At this point, the tissue anchor insertion instrument 100 can then be re-located for a further attempt to properly locate the anchor unit 30.

If it is determined that the position of both the anchor unit 30 and the blades 64 are correct, the trigger lever 112 can be squeezed further a set amount to move the plunger 110 and rotatable shaft 116 to slot position C. FIG. 7 best shows the tissue anchor insertion instrument 100 after the trigger lever 112 has been further squeezed to slot position C thereby fully extending the plunger 110 and the rotatable shaft 116. At slot position C, the spring clip 124 secured to the plunger 110 extends beyond and out of the distal end 106 of the barrel 104 thereby releasing the anchor unit 30 from the tissue anchor insertion instrument 100. The tissue anchor insertion instrument 100 can then be removed from the patient.

After delivering an anchor unit 30 to a fixation site, the tissue anchor insertion instrument 100 can be re-loaded with a new anchor unit 30 thus allowing the surgeon to install multiple anchor units into the same or multiple appropriate fixation sites.

It is also contemplated that the plunger arrangement could include any structure for allowing the anchor unit 30 to be selectively linearly translated and deployed through the guiding slot 108 of the barrel 104 of the tissue anchor insertion instrument 100 of the present teachings. For example, the plunger arrangement could include a plunger and a rotatable shaft which can reciprocate with respect to each other within the guiding slot 108 (i.e. not in unison) in a manner so as to selectively linear translate and deploy the anchor unit.

Figure 8:
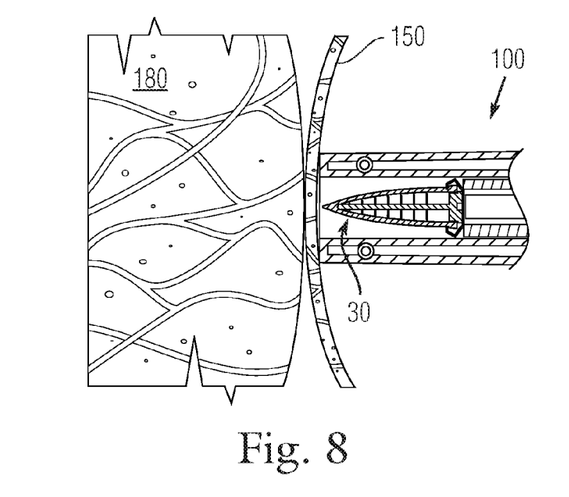
FIGS. 8-10 illustrate concurrent steps of using the tissue anchor insertion instrument and an anchor unit of the present teachings to suspend a vaginal wall.
Figure 9:
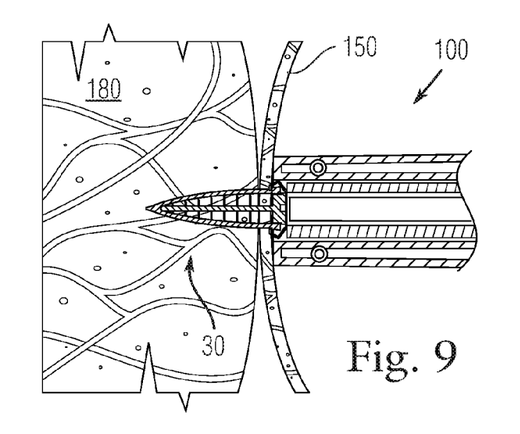
Figure 10:
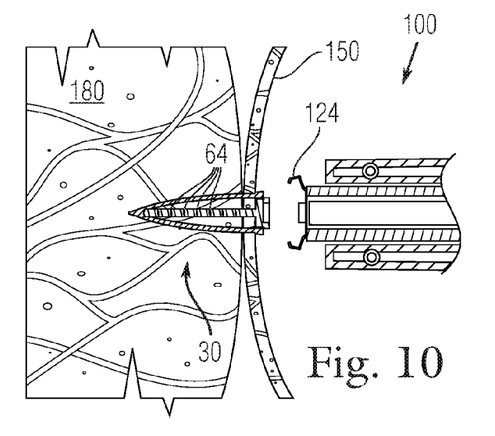

FIGS. 8-10 illustrate several procedural steps for the use of the anchor unit 30 and tissue anchor insertion instrument 100 of the present teachings to suspend a top vaginal wall 150 to the iliococcygeus muscle and fascia and/or sacrospinous ligament 180 to surgically treat vaginal vault prolapse and/or uterine prolapse in conditions of utero-vaginal prolapse.

In FIG. 8, the distal end of the tissue anchor insertion instrument 100 is shown already inserted into a vagina and positioned so that it pushes against one side of the falling (or prolapsed) vaginal wall 150 (also known as the vaginal vault). The falling vaginal wall 150 is shown being pushed up against the iliococcygeus muscle and fascia and/or sacrospinous ligament 180 by a distal end of the tissue anchor insertion instrument 100.

Figure 11:
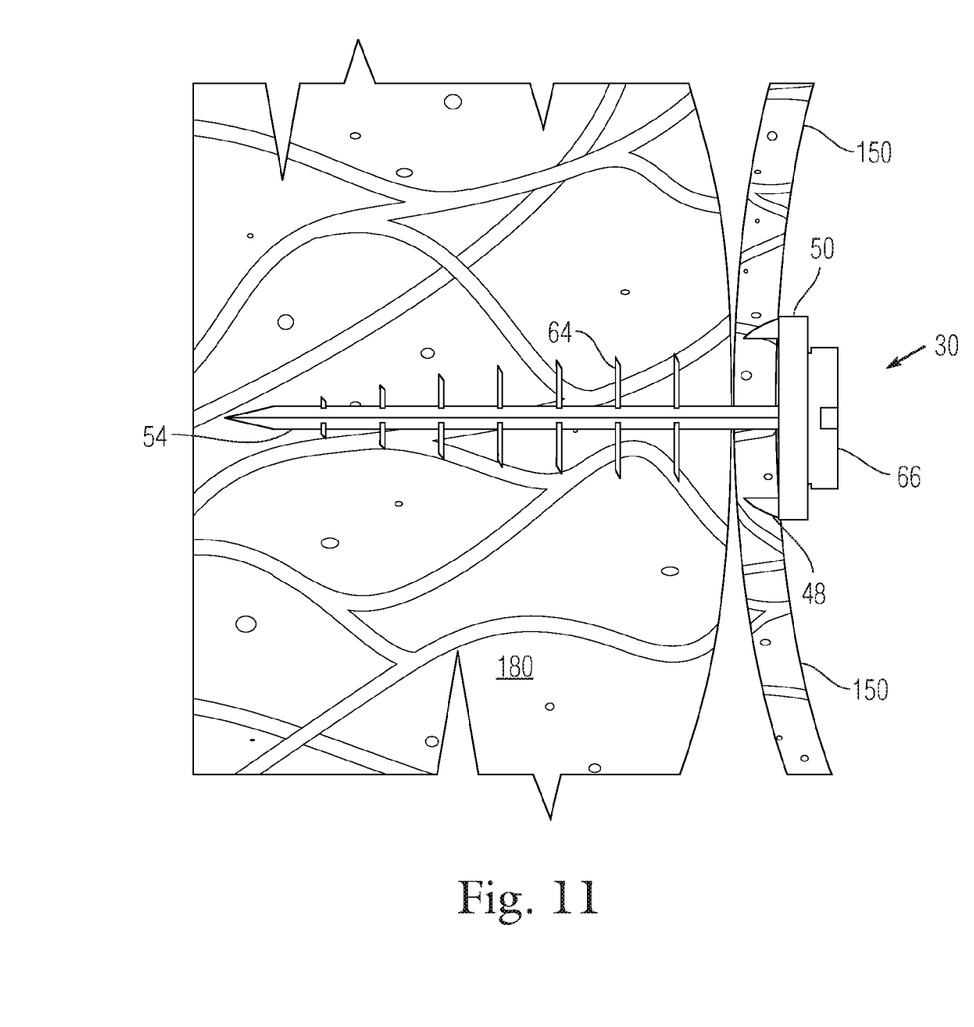
FIG. 11 shows a partial cross-sectional top view of a deployed anchor unit of the present teachings anchoring a vaginal wall.

As shown in FIG. 9, once the distal end of the tissue anchor insertion instrument 100 is correctly positioned with respect to vaginal wall 150, the trigger lever 112 of the tissue anchor insertion instrument 100 is pulled so that the anchor unit 30 is slowly advanced to penetrate through the vaginal wall 150 and into the iliococcygeus muscle and fascia and/or sacrospinous ligament 180 to a predetermined depth. As best shown in FIG. 11 which illustrates a top view of a deployed anchor unit 30, in a fully inserted position of the anchor unit 30, the base 50 and head 66 of the anchor unit 30 are arranged substantially flush with the vaginal wall 150 similar to the head of a nail after it has been hammered into sheetrock.

During the advancement of the anchor unit 30 into the tissue, the surgeon can keep his fingers on the trigger lever 112 to ensure that no rectal perforation has occurred. Should need arise, the surgeon can push back on the trigger lever 112 to retract the anchor unit 30 from the tissue.

Now referring to FIG. 10, when the surgeon has determined that the anchor unit 30 has been inserted into the proper location within the vaginal vault, the surgeon can rotate the turning knob 118 downwardly. As discussed above, this deploys the blades 64 of the anchor blade assembly 60 into the iliococcygeus muscle and fascia and/or sacrospinous ligament 180. The trigger lever 112 can then be squeezed further so that the spring clip 124 releases the anchor unit 30 from the tissue anchor insertion instrument 100.

As shown in FIG. 11, which illustrates a top view of the deployed anchor unit 30, a falling vaginal wall 150 can be securely anchored and suspended to the iliococcygeus muscle and fascia and or sacrospinous ligament 180 by way of the deployed anchor unit 30, thus correcting the prolapse. Moreover, one or more spikes 48 formed on the anchor base 50 can operate to securely hold the anchor unit 30 to the vaginal wall 150 and to prevent the slit in the vaginal wall 150 formed by the insertion of the anchor unit 30 from opening. The anchor unit 30 can be designed to eventually dissolve leaving behind enough scarring to hold the vagina wall 150 in this position.

The same single or multiple anchor insertion procedure can be performed again on the opposite side of the vaginal vault using another anchor unit 30 and deployed using the tissue anchor insertion instrument 100 of the present teachings.

The present teachings can be used as a primary surgical procedure for the repair of diagnosed vaginal vault prolapse, or to repair and/or prevent vaginal prolapse diagnosed at the time of vaginal hysterectomy and/or prolapse repair. In addition, the present teachings can be used to treat or prevent uterine prolapse at the time of prolapse repair. The tissue anchor insertion instrument 100 of the present teachings can also be used to remove a previously inserted anchor unit 30 post-operatively.

Those skilled in the art can appreciate from the foregoing description that the present teachings can be implemented in a variety of forms. Therefore, while these teachings have been described in connection with particular embodiments and examples thereof, the true scope of the present teachings should not be so limited. Various changes and modifications may be made without departing from the scope of the teachings herein.

What is claimed is:

1. An anchor unit implant for the repair of body tissue comprising:

an anchor housing including a first peripheral wall and a second peripheral wall each including a sharp edge along an outer portion of the respective peripheral wall, the first peripheral wall and the second peripheral wall being laterally spaced from each other at a proximal end and converging into a sharp tip at a distal end such that the anchor housing is arranged in the shape of a knife blade; and an anchor blade assembly rotatably arranged with respect to the anchor housing and including a plurality of blades rigidly connected with a main shaft, the main shaft being rotatably arranged between the first and second peripheral walls of the anchor housing;

wherein the anchor blade assembly is capable of being rotated with respect to the anchor housing from (i) a non-deployed state in which the plurality of blades are co-planar with the first and second peripheral walls of the anchor housing whereby the anchor unit implant can penetrate an area of body tissue to be repaired into (ii) a deployed state in which the plurality of blades extend beyond a plane defined by the first and second peripheral walls of the anchor housing and cut into body tissue to secure the anchor unit implant to the body tissue to be repaired; and wherein the anchor blade assembly is capable of being rotated with respect to the anchor housing from the deployed state back into the non-deployed state in which the plurality of blades are co-planar with the first and second peripheral walls of the anchor housing and the anchor unit implant is then removable from the area of body tissue to be repaired and re-positionable.

2. The anchor unit implant of claim 1, wherein the plurality of rigidly connected blades extend perpendicularly with respect to a longitudinal axis of the rotatable main shaft of the anchor blade assembly.

3. The anchor unit implant of claim 1, wherein the plurality of blades, the main shaft being configured to be rotatably supported by the anchor housing the plurality of rigidly connected blades include at least one blade extending from one side of the rotatable main shaft and at least one blade extending from an opposite side of the rotatable main shaft in a co-planar arrangement.

4. The anchor unit implant of claim 1, wherein the anchor housing includes an anchor base and the proximal end of the first peripheral wall and the second peripheral wall extend from the anchor base.

5. The anchor unit implant of claim 4, wherein the anchor blade assembly is rotatably supported by the anchor base.

6. The anchor unit implant of claim 5, wherein the anchor base includes at least one spike.

7. The anchor unit implant of claim 4, wherein the anchor blade assembly includes a head and the main shaft extends from the head, the head being rotationally arranged with respect to the anchor base.

8. The anchor unit implant of claim 7, wherein the head of the anchor blade assembly includes threads that are engageable with corresponding threads in the anchor base.

9. The anchor unit implant of claim 1, wherein the anchor blade assembly is configured to be engageable with an instrument to allow the anchor blade assembly to be selectively movable with respect to the anchor housing.

10. The anchor unit implant of claim 1, wherein the anchor blade assembly is configured to be rotationally supported within the first and second peripheral walls of the outer anchor housing.

11. The anchor unit implant of claim 1, wherein at least one of the anchor housing and the anchor blade assembly are made from a biodegradable material.

\* \* \* \* \*